United States Patent
Boggs et al.

(10) Patent No.: US 6,372,021 B1
(45) Date of Patent: Apr. 16, 2002

(54) EXTRACTIVE REMOVAL OF METHANOL FROM CUMENE-TO-PHENOL PROCESS VENT GAS

(75) Inventors: David L. Boggs, Mt. Vernon, IN (US); Paul William Buckley, Scotia, NY (US); Andrew H. Farrell, Mt. Vernon, IN (US); John William Fulmer, Mt. Vernon, IN (US); Bradley Norman Geyer, Mt. Vernon, IN (US); William Dale Kight, Poseyville, IN (US); Tara H. Wight, Voorheesville, NY (US)

(73) Assignee: General Electric Company, Pittsfield, MA (US)

( * ) Notice: Subject to any disclaimer, the term of this patent is extended or adjusted under 35 U.S.C. 154(b) by 56 days.

(21) Appl. No.: 09/659,352

(22) Filed: Sep. 12, 2000

(51) Int. Cl.$^7$ ................................................ B01D 50/00
(52) U.S. Cl. .............................. 95/92; 568/749; 95/228
(58) Field of Search ............................ 95/92, 288, 228; 96/134, 267; 423/245.1; 568/749, 742, 748

(56) References Cited

U.S. PATENT DOCUMENTS

| | | |
|---|---|---|
| 3,232,029 A * | 2/1966 | Evans, Jr. |
| 3,981,156 A | 9/1976 | Modisette et al. |
| 4,239,508 A * | 12/1980 | Rock et al. |
| 4,375,976 A | 3/1983 | Potter |
| 4,511,379 A | 4/1985 | Hauptmann |
| 4,588,535 A | 5/1986 | Foidl |
| 4,734,108 A | 3/1988 | Cox et al. |
| 4,948,402 A | 8/1990 | Davis |
| 4,966,611 A * | 10/1990 | Schumacher et al. |
| 5,122,165 A * | 6/1992 | Wang et al. |
| 5,154,735 A * | 10/1992 | Dinsmore et al. |
| 5,186,728 A | 2/1993 | Fong |
| 5,371,305 A | 12/1994 | Hood |
| 5,375,562 A | 12/1994 | Brinck et al. |
| 5,430,200 A | 7/1995 | Hood |
| 5,614,159 A | 3/1997 | Modic et al. |
| 5,891,410 A | 4/1999 | Modic et al. |
| 5,891,411 A | 4/1999 | Gribbon |
| 5,907,066 A | 5/1999 | Wachs |
| 5,968,235 A | 10/1999 | Grime et al. |

\* cited by examiner

*Primary Examiner*—Duane S. Smith
(74) *Attorney, Agent, or Firm*—Oppedahl & Larson LLP

(57) ABSTRACT

Injection of even very small amounts of supplemental water to the spent-air stream at points upstream from the heat exchanger cooler(s) used in processing spent-air streams from a cumene-to-phenol process allows these heat exchanger coolers to act as both extractors and condensers. It is therefore possible to recover from the heat exchanger cooler a methanol/water condensate, thereby substantially reducing the amount of methanol in the spent-air stream prior to discharge. Thus, known methods for manufacture of phenol from cumene in which an oxygen-containing gas stream is passed through liquid cumene to produce an oxidate product and a spent-air stream comprising methanol and cumene and a saturating amount of water; and in which the spent-air stream is passed through one or more heat exchanger coolers and a carbon bed prior to discharge can be improved.

8 Claims, 1 Drawing Sheet

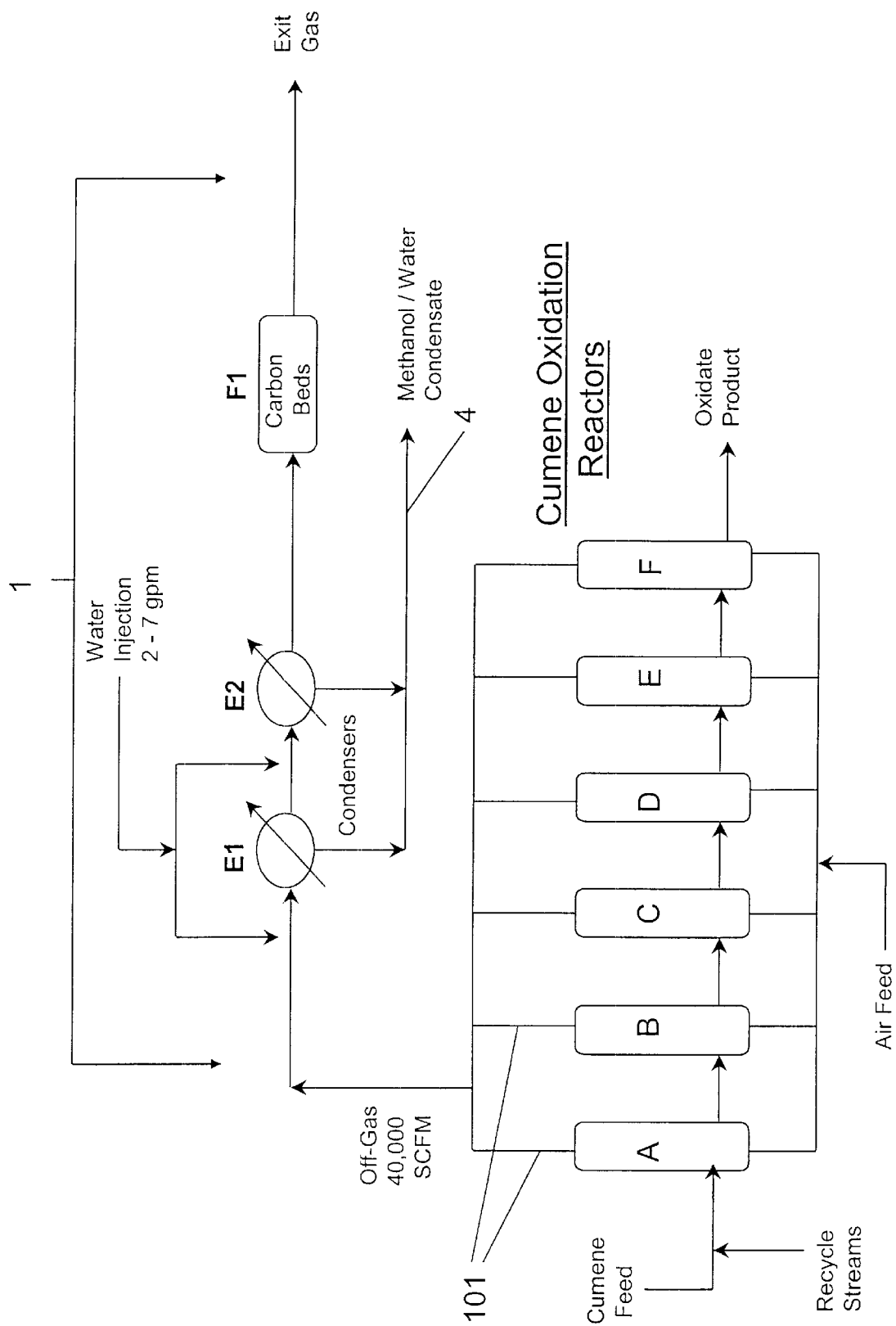

EXTRACTIVE REMOVAL OF METHANOL FROM CUMENE-TO-PHENOL PROCESS VENT GAS

BACKGROUND OF THE INVENTION

This application relates to a method for removing methanol from vent gas streams generated in a cumene-to-phenol process.

In the well known cumene-to-phenol process, methanol is produced as a minor by-product during the cumene oxidation reaction step. Several reactor designs exist in the industry today in which the reaction is typically conducted at 70–130° C. and 20–120 psig. In these processes, air is continuously introduced into liquid cumene contained in multiple gas-sparged towers or tanks. The oxygen in the air serves as raw material to produce the desired intermediate product, cumene hydroperoxide. The nitrogen contained in the air feed stream along with 1–10% residual oxygen exits the top of each of the reactors. This "spent air" stream is saturated with water, cumene and contains other trace volatile organic compounds (VOC's) including methanol. Prior to venting, the current standard practice is to pass this "spent air" stream through a series of heat exchanger coolers, refrigerated condensers and activated carbon adsorption beds to recover the cumene value contained therein and to prevent VOC emissions to the environment.

It is widely recognized in the industry that the activated carbon adsorption beds mentioned above are ineffective in removing the methanol component and a majority of the methanol contained in the "spent air" stream passes through the beds unadsorbed. Also the vent gas coolers and refrigerated condensers provided in the standard designs are not effective in condensing the methanol from the "spent air" vent gas stream due to its high volatility and due to the fact that the very large volume "spent air" stream passes through these shell-and-tube exchangers at very high velocity resulting in poor heat transfer and poor condensation efficiency. This serious hazardous air pollutant (HAP) emission problem impacts all cumene-to-phenol producers today; and expensive and complicated downstream control devices must be installed in these plants to adequately control and reduce methanol emissions. Such VOC control devices include expensive thermal incinerators, catalytic oxidation incinerators and special gas-scrubbing columns.

U.S. Pat. No. 5,891,411 (Gribbon) and U.S. Pat. No. 5,375,562 (Brinck) decribe catalytic combustion methods utilizing a regenerative catalytic oxidizer unit for purifying exhaust gases from chemical processes to remove volatile organic compounds including methanol. This process is effective but requires a high capital investment for the unique equipment, including special multi-pass heat exchangers and catalyst. This method also risks the formation of undesirable NOX pollutant due to the high operating temperatures required. U.S. Pat. No. 5,907,066 (Wachs) describes the use of a special metal oxide catalytic process to convert methanol in waste vent gas to formaldehyde. This method is also costly due to catalyst plus the conversion of methanol to formaldehyde is not desirable because it is a harmful VOC pollutant.

U.S. Pat. No. 5,891,410 (Modic) describes a process for the purification of an off-gas containing methanol which originates from oxidation of xylene with air. However in this case special solvents are employed and expensive countercurrent multi-stage extraction columns are required in order to remove the methanol to low levels. Similar and even more complicated and expensive scrubber-extraction systems for removal of VOC's from vent gases using water are described in U.S. Pat. Nos. 5,186,728, 4,948,402 and 4,734,108. All of these methods suffer due to high investment cost coupled with complicated operation.

Thus, there remains a need for process improvements which will facilitate the removal of methanol from cumene-to-phenol process vent gases at reasonable cost.

SUMMARY OF THE INVENTION

It has now been surprisingly discovered that injection of even very small amounts of supplemental water to the spent-air stream at points upstream from the heat exchanger cooler(s) allows these heat exchanger coolers to act as both extractors and condensers. It is therefore possible to recover from the heat exchanger cooler a methanol/water condensate, thereby substantially reducing the amount of methanol in the spent-air stream prior to discharge. Thus, the invention provides an improvement to known methods for manufacture of phenol from cumene in which an oxygen-containing gas stream is passed through liquid cumene to produce an oxidate product and a spent-air stream comprising methanol and cumene and a saturating amount of water; and in which the spent-air stream is passed through one or more heat exchanger coolers and a carbon bed prior to discharge. The improvement comprises the steps of injecting a supplemental amount of water into the spent air stream at one or more points upstream from at least one of the one or more heat exchanger coolers, and recovering a methanol/water condensate from the heat exchanger coolers, thereby reducing the methanol content of the spent-air stream prior to discharge.

BRIEF DESCRIPTION OF THE DRAWING

FIG. 1 shows a schematic representation of a facility for manufacture of phenol from cumene in accordance with the invention.

DETAILED DESCRIPTION OF THE INVENTION

The present invention provides a simple, inexpensive, and novel method which allows fall recovery of the cumene value contained in the "spent air" vent stream from a cumene-to-phenol process, while at the same time effectively removing the methanol component to very low levels to provide the required emissions control. It has been found that a controlled addition of a small amount of supplemental water into the "spent air stream" just prior to its introduction into the coolers and refrigerated condensers greatly enhances the performance of these exchangers and provides an effective method of methanol removal by initiating a water-extraction and condensation-removal process within the condensers themselves.

As used in the specification and claims of this application, the term "water" refers to the molecular species "$H_2O$". The water may be injected into the process in the form of a liquid or as steam. The term "supplemental water" refers to additional water added to the spent-air stream. It will be appreciated that the amount of water in the spent-air stream will vary with process conditions such as temperature and pressure, and the location within the spent-air processing line (decreasing after each heat exchanger cooler/condenser passage). Addition of "supplemental water" refers to addition of water to the spent-air stream in the spent-air processing line to a level which is higher than would be present in the absence of such addition.

FIG. 1 provides a schematic representation of a plant for carrying out a cumene-to-phenol process with the improvements of the present invention. Cumene (isopropylbenzene) is fed to a series of vertical reactors ( A thru F ) arranged in series operating at a 70–120° C. temperature range and 70–100 psig pressure. The use of six reactors is not required, and the number of reactors in excess of one is a matter of design choice depending on the desired capacity of the plant and the size of the individual reactors. An oxygen-containing gas (for example air) is fed into the bottom of each of the gas-sparged reactors and the liquid cumene and gaseous oxygen mix and chemically react to form the desired cumene hydroperoxide (CHP) product along with several by-products which include dimethylbenzyl alcohol (DMBA), acetophenone (AP), and methanol. This liquid oxidate product mixture exits the last reactor (F in FIG. 1) and passes downstream for further processing to phenol and acetone. Additionally as shown in FIG. 1, several recycle streams may feed into the cumene oxidizer reactor train along with the fresh cumene. These recycles contain mainly water and cumene for recovery.

During the cumene oxidation process a "spent air" vapor stream is generated which exits the top of each of the oxidation reactors (A–F) via collector lines 101. This spent-air stream contains residual oxygen not consumed during the reaction, typically 1–10 vol %, plus any inert nitrogen contained in the incoming air feed stream. This "spent-air" vapor stream is also saturated with cumene and water and contains methanol and VOC as contaminants. The concentrations of these materials is variable and is dependent on the reaction conditions employed which influences their partial pressure and volatility.

The "spent air" streams from each of the reactors is combined into one large vapor stream in spent-air processing line 1 and directed through a series of heat exchanger coolers (E1, E2) for condensation and removal of the cumene present. The number of heat exchanger coolers in excess of one is a design choice which depends on the efficiency of an individual heat exchanger cooler and the required characteristics of the exit gas. These coolers can employ water and/or refrigerants to improve performance. The resulting recovered wet cumene condensate stream flows by gravity from the bottom of the coolers and is typically recycled to the oxidation reactors for recovery through condensate collection line 4. Next, the "spent-air" gas stream passes through activated carbon beds (F1) to remove the final traces of cumene and other VOC prior to its discharge as "exit gas" to the atmosphere and environment.

Unfortunately the majority of the methanol component contained in the "spent air" stream is not removed during the above described normal practice of condensation and carbon adsorption treatment, and it remains as a VOC contaminant in the "exit gas" discharged to the atmosphere. However in the present process it has now been discovered that the methanol can be effectively removed from the very large "spent air" stream by addition of a small amount of supplemental water into the feed inlet of the existing coolers E1 and E2. The supplemental water or steam extractant can be added to either E1 or E2 alone, or in combination to both E1 and E2 which is the preferred process. Thus the E1 and E2 exchangers are made to serve both as extractors and condensers so that this equipment already in place for needed cumene recovery is also made to function as efficient gas extractors and methanol contaminant devices. Thus no additional investment is required for methanol containment equipment and the fall amount of the valuable cumene contained in the "spent air" stream is recovered without penalty.

Because cumene is insoluble in water, the condensate recovered in condensate collection line 4 has two phases: a top organic (cumene) phase and a bottom (aqueous) phase which are easily separated. Conventionally, a portion of the bottom (aqueous) phase is removed, for example using a settling drum at the end of condensate collection line 4, with about 50% of the water being recycled along with the cumene and combined with the cumene feed. This same type of separation is performed in the method of the invention, although it may be desirable to remove a greater portion of the bottom (aqueous) phase, for example 75%, to reduce the amount of methanol introduced into the feed stream. This separated methanol/water is then processed through an appropriate liquid waste handling system such as a BioTreatment plant. agent is added at multiple points, including an addition to the "spent air" stream exiting the first heat exchanger cooler (E1) after the bulk of the in-situ water has been removed. An addition at this point provides an increase in the amount of water in the "spent air" stream and gives a very effective 2nd stage of extraction within the subsequent cooler. Preferably, the amount of water added at the second stage is sufficient to resaturate or even somewhat oversaturate the spent-air stream.

A surprising aspect of this invention is the very small amount of supplemental water required to provide the dramatic improvement. Furthermore, no special gas-liquid contacting devices or multi-stage scrubber-type columns are required to obtain the dramatic VOC reduction. For example, a 2–7 gpm flow of water injected into the 40,000 SCFM "spent air" stream has been shown to reduce methanol concentration from >500 ppm to <50 ppm. It will be appreciated that not all facilities will be operated at the same flow rate for the spent-air stream. Thus, in a general sense, the water is injected at a rate of from about 0.00005 to 0.0002 gallons per standard cubic foot of spent-air.

Achieving such an substantial methanol reduction utilizing this very small (water:gas) extraction ratio is quite unexpected based on mass balance considerations and such performance would normally be expected only if one used expensive multi-stage extractor columns operating with large volumes of extractant. However in our present invention the existing heat exchangers are made to act as both extractors and condensers so only the existing equipment is needed and no additional capital investment is required.

While the foregoing discussion focuses on a cumene-to-phenol process, the same process improvement could be incorporated into other processes which produce a spent-air stream containing methanol and water-insoluble organics that are recovered by condensation. Thus, a further aspect of the invention is a method for removing methanol from a spent-air stream comprising methanol, a water insoluble organic compound and an initial amount of water. In accordance with this method, a supplemental amount of water is injected into the spent-air stream. The spent-air stream and supplemental water are then passed through a heat exchanger cooler; and a condensate containing the water-insoluble organic and a methanol/water mixture from the spent-air stream is recovered.

The following examples are provided to illustrate the present invention, but are not meant to limit its scope:

Example No. 1 (Comparative)

A commercial cumene oxidation process operates continuously as depicted in FIG. 1 but without addition of supplemental water, at 80–120° C. reaction temperature and 70–90 psig pressure, with a very large 40,000 SCFM "spent air" gas stream being generated as part of the normal operation. A gas chromatographic analysis of the spent-air stream prior to the first heat exchanger cooler E1 gave the following composition:

| | |
|---|---|
| Oxygen, vol % | 3.5 |
| Nitrogen, vol % | 89–91 |
| Water, vol % | 7.5 |
| Cumene, ppmv | 800 |
| Methanol, ppmv | 300 |

Simultaneous sampling and chromatographic analysis of the "exit gas" stream gave the following composition:

| | |
|---|---|
| Oxygen, vol % | 3.5 |
| Nitrogen, vol % | 91–94 |
| Water, vol % | 3.0 |
| Cumene, ppmv | <20 |
| Methanol, ppmv | 290 |

A comparison of the above sampling results shows that the 300 ppm contained methanol is not effectively removed by condensation and carbon treatment of the "spent air" stream when no supplemental water is added to the E1 and E2 shell-and-tube type condensers.

Example No. 2

A three day plant trial was conducted utilizing the process of Example No. 1, but with supplemental water addition provided to the feed inlets of both of the existing shell-and-tube exchanger/coolers E1 and E2. In this trial 2.5 gpm of water was added to the E1 condenser inlet stream and 5.0 gpm water was added to the inlet of the E2 condenser. No special vapor-liquid contacting or mixing devices were employed. During this trial period a total of 133 samples of the exit gas were analyzed by an in-line process gas chromatograph. Measurements were also taken on gas from between the two heat exchangers E1 and E2. The supplemental water addition and extraction provided a significant reduction (i.e. 52.8%) in methanol content as the data below shows:

| | |
|---|---|
| before first heat exchanger | 301 ppm methanol |
| between heat exchangers | 150 ppm methanol |
| exit gas | 141 ppm methanol |

Example No. 3

A two day plant trial was conducted utilizing the process of Example No.2 with supplemental water addition, during which time 87 samples of the "exit gas" stream were analyzed by an in-line process gas chromatograph. The methanol content was reduced from 341 ppm concentration before the first heat exchanger, down to a 142 ppm concentration in the exit gas, representing a 58.4% removal efficiency.

Example No. 4

Another two day plant trial was conducted with supplemental water addition according to the process of Example No. 2, during which time 41 samples were analyzed. The methanol content was successfully reduced from 287 ppm down to 127 ppm which achieves a 55.6% methanol removal efficiency when comparing the initial spent-air stream to the exit gas.

What is claimed is:

1. In a method for manufacture of phenol from cumene, wherein an oxygen-containing gas stream is passed through liquid cumene to produce an oxidate product and a spent-air stream comprising methanol and cumene and an initial amount of water; and wherein the spent-air stream is passed through one or more heat exchanger coolers and a carbon bed prior to discharge, the improvement comprising:
   injecting a supplemental amount of water into the spent air stream at one or more points upstream from at least one of the one or more heat exchanger coolers, and
   recovering a methanol/water condensate from the heat exchanger coolers, thereby reducing the methanol content of the spent-air stream prior to discharge.

2. The improvement of claim 1, wherein the water is injected at a rate of from about 0.00005 to 0.0002 gallons per standard cubic foot of spent-air.

3. The improvement of claim 1, wherein two heat exchanger coolers are used, and wherein water is injected at two points, one point upstream from the first of the two heat exchanger coolers, and a second point upstream from the second of the two heat exchanger coolers, but downstream from the first of the two heat exchanger coolers.

4. The improvement of claim 3, wherein the water is injected at each of the two points at a rate of about 0.00005 to 0.0002 gallons per standard cubic foot of spent-air.

5. A method for removing methanol from a spent-air stream comprising methanol, a water insoluble organic compound and an initial amount of water, said method comprising the steps of:
   (a) injecting a supplemental amount of water into the spent-air stream;
   (b) passing the spent-air stream and supplemental water through a heat exchanger cooler; and
   (c) separating a condensate containing the water-insoluble organic and a methanol/water mixture from the spent-air stream.

6. The method of claim 5, wherein the water-insoluble inorganic is cumene.

7. The method of claim 6, wherein the water is injected at a rate of from about 0.00005 to 0.0002 gallons per standard cubic foot of spent-air.

8. A facility for the manufacture of phenol by oxidation of cumene comprising:
   (a) at least one vertical reactor;
   (b) a source of cumene;
   (c) a feed line connecting the vertical reactor to the source of cumene;
   (d) an air feed line connected to the vertical reactor for introducing oxygen-containing gas into the bottom of the vertical reactor;
   (e) a spent-air collection line connected to the vertical reactor for collecting a spent-air stream from the top of the vertical reactor;
   (f) a spent air processing line connected to the spent air collection line, said spent-air processing line transporting the collected spent-air stream through at least one heat exchanger cooler and an activated carbon bed;
   (g) a water injection line connected to a source of water and to the spent air processing line at a point upstream from the heat exchanger cooler; and
   (h) a condensate collection line connected to the heat exchanger cooler.

* * * * *